United States Patent [19]

Cornwell

[11] Patent Number: 5,040,904
[45] Date of Patent: Aug. 20, 1991

[54] INFECTIOUS/MEDICAL WASTE CONTAINMENT CARRIER

[75] Inventor: James T. Cornwell, Rome, Ga.
[73] Assignee: Gene D. Hoffman, Wayzata, Minn.
[21] Appl. No.: 453,761
[22] Filed: Dec. 20, 1989
[51] Int. Cl.$^5$ ............................................. B65D 33/28
[52] U.S. Cl. ........................................ 583/71; 383/40; 383/62; 383/121
[58] Field of Search ...................... 383/61, 62, 70, 71, 383/39, 40, 121

[56] References Cited

U.S. PATENT DOCUMENTS

| | | | |
|---|---|---|---|
| 684,573 | 10/1901 | Howe | 383/62 |
| 956,941 | 5/1910 | Chapman | 383/62 |
| 1,052,379 | 2/1913 | Ranken et al. | 383/71 X |
| 1,191,051 | 7/1916 | Wichmann | 383/62 |
| 2,723,936 | 11/1955 | Ryan | 383/107 X |
| 3,369,584 | 2/1968 | Faccio et al. | 383/61 |
| 3,439,867 | 4/1968 | Paxton | 383/62 |
| 3,481,461 | 12/1969 | Paxton | 383/62 X |
| 3,485,697 | 12/1969 | Reed | 383/40 X |
| 3,519,196 | 7/1970 | Paxton | 383/62 |
| 3,565,738 | 2/1971 | Kirkpatrick | 383/62 |
| 4,008,851 | 2/1977 | Hirsch | 383/62 |
| 4,658,433 | 4/1987 | Savicki | 383/107 X |

Primary Examiner—Stephen P. Garbe
Assistant Examiner—Jes F. Pascua

[57] ABSTRACT

This invention, Infections/Medical Waste Containment Carrier, is a manufactured, flexible container in which solid and/or liquid infectious/medical waste is placed for containment, storage, transport and incineration. The Infectious/Medical Waste Containment Carrier consists of three integral functional components:

1. A coextruded polyethylene tube with walls of a given thickness.
2. A closure pouch with a self-contained tie cord.
3. A bottom seal of dual thermo-sealed bars with enforced cross members and air pockets.

Once the bottom seal is applied to the coextruded polyethylene tube the tube becomes a bottom closed container. When the pouch is applied at a specific position located in the center and near the top of the containment carrier and the bottom and top are serrated, the containment carrier is constructed to serve as a depository for infectious/medical waste.

Once the infectious/medical waste is deposited in the containment carrier, the closure pouch opened and the tie cord is applied as directed, the Infectious/Medical Waste Containment Carrier becomes a self-contained atmosphere that will not allow the emission of solid, liquid or gas infectious/medical wastes.

The Infectious/Medical Waste Containment Carrier's walls are manufactured from a combination of polyethylene polymers that when incinerated will not emit environmentally damaging gases. These polymers when coextruded from a wall of the containment carrier that is highly resistant to puncture and provides a high degree of structural integrity.

4 Claims, 4 Drawing Sheets

INFECTIOUS/MEDICAL WASTE CONTAINMENT CARRIER

References Cited

| U.S. Pats. | |
|---|---|
| U.S. Pat. No. | Class |
| 3,519,196 | 229/62 |
| 4,705,174 | 206/632 |
| 3,565,738 | 161/38 |
| 4,008,851 | 229/62 |
| 4,051,994 | 229/65 |
| 4,159,077 | 383/94 |
| 3,779,139 | 383/77 |
| 4,706,289 | 383/71 |

BRIEF SUMMARY OF THE INVENTION

This invention, Infectious/Medical Waste Containment Carrier consists of three integral functional components. A coextruded polyethylene tube with walls at a given thickness. A closure pouch, thermo-sealed to the outer wall of the containment carrier containing a twelve (12) inch, fifty (50) pound test cord. The center of the cord is welded to the inside back of the pouch, so that when the top of the pouch is torn away each side of the cord will fall free. A bottom seal, consisting of a dual thermo-sealed bars and enforcements with spaced air-pockets. These air pockets provide strength and insure that should the upper seal bar fail, at any point across the web of the containment carrier, the air-pockets will serve as collectors of any infectious/medical waste residue liquid seepage.

The functional coextruded polyethylene containment carrier's walls are constructed of a combination of polymers that are highly resistant to puncture and offer a high degree of structural integrety including resistance to rupture at impact and elongation strength. The polymers also provide barriers to protect from emission of odors and harmful gases that may be created by the infectious/medical waste.

The closure pouch containing the tie closure cord is welded to the structure of the pouch which is welded to the composition of the wall of the containment carrier. The pouch can be opened with a "quick zip" of the tab which removes the top cover of the pouch, releasing the closure cord. With the infectious/medical waste deposited in the containment carrier, the containment carrier is then twisted using the containment carrier's walls above the top level of the deposited infectious/medical waste until the twist forms a tightly drawn extension of the containment carrier that is then folded in an inverted "V" and is tightly wrapped with the closure cord, then a series of overhand knots are tied to insure the closure is leak-proof.

The seal when in place is positioned a short space from the bottom opening of the containment carrier. Once the seal is applied to the containment carrier, the bottom is such that the inner and outer walls of the containment carrier are fused into one entity. The seal is composed of thermo-sealed areas and added-strength air-pockets. This combination provides a seal that is fail-proof for the prevention of emission of infectious/medical waste—solids, liquids or gases.

BACKGROUND

This invention, Infections/Medical Waste Containment Carrier, provides a self-contained atmosphere for the containment of two (2) to four (4) pounds of infections/medical waste generated by a medical facility (hospital, laboratory, blood bank, clinic, practicing physician or dentist, ambulatory surgery center, nursing home and/or home care center and medical research facility). According to an article published in the Sept. 22/29, 1989, Vol. 262, No. 12 issue of the *Journal of the American Medical Association* entitled "Management of Infectious Waste by U.S. Hospitals", approximately 23.9 million pounds of infectious waste is generated by hospitals each day in some 13,600 hospitals (public and private) in the United States. The estimate for infectious/medical waste generated by medical laboratories (4,916); blood banks (4,189); nursing and personal care facilities (889); skilled nursing care facilities (6,921); nursing and personal care facilities, NEC. (6,522); offices of health practitioners (11,767); outpatient facilities (9,344); physician's offices (172,857); and dentists offices (94,994) is approximately 18.7 million pounds per day. The total infectious/medical waste generated per day in 1987 was 42.6 million pounds.

The term medical facility waste, medical waste and infectious waste are often used inappropriately as synonymons. The term medical facility waste refers to all solid waste (biologic or nonbiologic) that is discarded and not intended for further use (eg, administrative waste, dietary waste and non-toxic medical waste); medical waste refers to toxic materials generated as a result of patient diagnosis, treatment or imunization (eg, soiled dressing and intravenous tubing); and infectious waste refers to that portion of medical waste that could transmit an infectious disease (eg, microbiological waste and "sharps").

Currently, the recommended procedure for the collection, containment and transport of infectious/medical waste is either one of three methods:

a. To utilize a 3 mil thick (or less thick) red opaque printed (wording and symbol) polyethylene plastic bag in which the infectious/medical waste is placed. The top of the bag is then twisted and tied in an overhand knot. The bag, once tied, containing between two (2) and four (4) pounds of infectious/medical waste is then placed in a corrugated box (generally 18"×18"×24") along with one to three other bags of infectious/medical waste. The box is sealed with tape and is labeled with wording and symbols. It is stored in a cool or refrigerated area, picked-up and transported to an incinerator.

b. To utilize a 1.5 mil thick red printed polyethylene plastic bag (printed as in "a" above) in which the two (2) to four (4) pounds of infectious/medical waste is placed. The bag is tied in an overhand knot as in "a" above. The bag is then inserted into another 1.5 mil thick red printed polyethylene bag and tied as in "a" above. The double bags are then placed in a corrugated box with one to three double bagged units and the procedure as in "a" above is then followed.

c. To utilize a 3 mil thick orange opaque printed (wording and symbol) polypropylene plastic bag, which is autoclavable, to contain and transport two (2) to four (4) pounds of infectious/medical waste. The bag containing the waste is tied off with a standard twist tie and then autoclaved, then moved to an incinerator.

There are problems, primarily with "a" and "b" procedures described above, that are identified below. These problems are based on interviews with personnel handling infectious/medical waste in 82 hospitals and 26 other medical facilities in the United States:
1. "We can never find a tie to close the bag."
2. "Nobody tells us how to close the bag. Certainly, what's in an infectious waste bag is a lot different than what's in a "Hefty" garbage bag."
3. "The bags we get don't have seals that don't break. We get four or five of these spills a week. It just means more labor costs to get the mess cleaned up. Blood stains are real bad."
4. "Bags we use ain't so you can't see through them. Its not very nice to see blood and guts. The bag should be so you can't see through it."
5. "It's stupid to put a bag in a bag then both bags in a box. That doesn't make good sense. We've got a little box that we place needles and broken glass in so it can go in a bag without making a hole in the bag. These things never get in a bag. Why doesn't somebody come up with one bag that'll do the job."
6. "Bags are too thin. The seal doesn't hold. We are really scared of getting some bug 'cause they break so often."
7. "Even with two bags, they still leak blood."
8. "You don't have to clean up old blood when one of those red bags pop-open. I do!"
9. "We pay about 40 cents for a bag and about $1.25 for the box. When you have to use two bags and a box, with sharps in another container, something needs to be done. $2.05 for a way to handle less than two pounds of infectious waste is too high. Plus, clean-up cost when the bag breaks."
10. "When the seal goes, the blood and mess goes everywhere."
11. "There's no way! Two bags and a box aren't the answer."
12. "What we need is a bag. A simple bag that will do the trick."

Thus, based on these comments which represent only a small but majority feeling of some 296 received in talking with people in 106 medical facilities, the Infectious/Medical Waste Containment Carrier has been developed.

BRIEF DESCRIPTION OF THE DRAWINGS

The drawings consist of nine (9) figure drawings with twenty-three (23) identifiable and defined segments. The drawings represent the concept of the invention; the construction of the invention and the details of the basic components that comprise the invention.

DETAILED DESCRIPTION OF THE DRAWINGS

Figure 1:
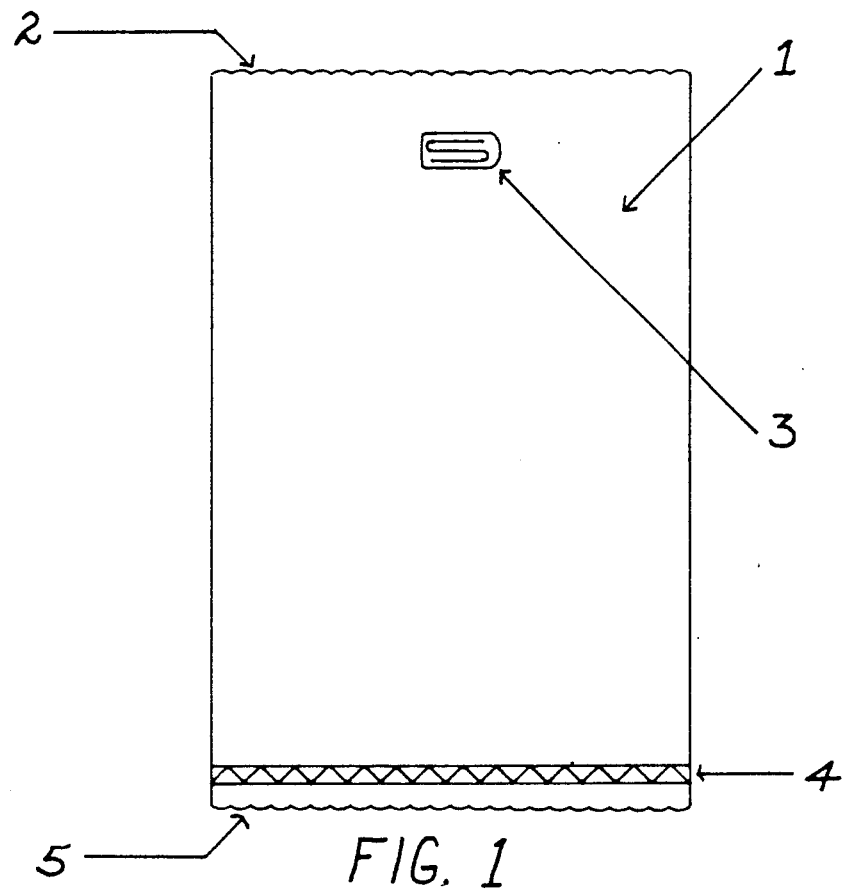
FIG. 1 is the overall concept of the Infectious/Medical Waste Containment Carrier which identifies the three basic components.

FIG. 1 illustrates the overall configuration of the Infectious/Medical Waste Containment Carrier. The outer wall or web of the containment carrier 1 is constructed as a tube from polyethylene materials prior to the application of bottom seal 4 just above the serration 5. This seal 4 insures a leak-proof, air-tight bottom of the containment carrier. The pouch 3 contains the closure cord which is used when the infectious waste is deposited in the containment carrier as the tie for fail-safe closure procedure.

Figure 2:
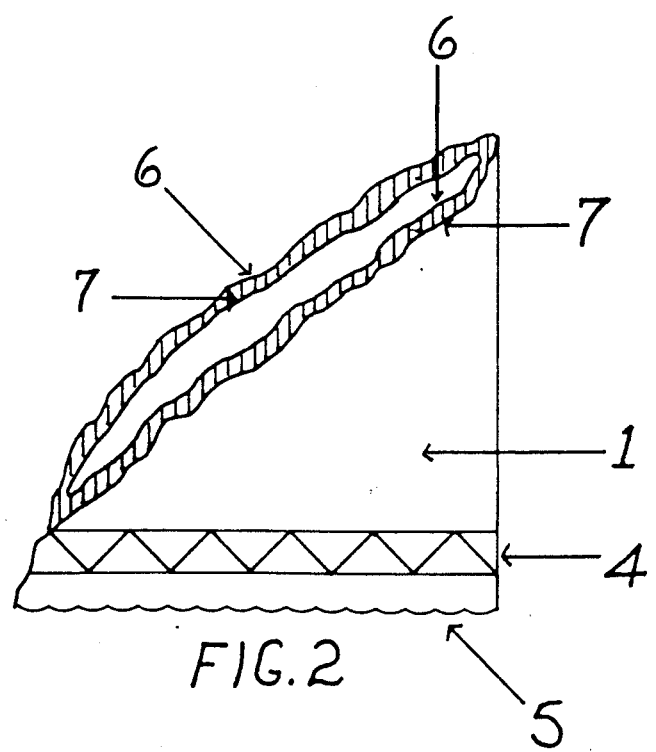
FIG. 2 is a cut-away of the wall's layers as to structural integrity.

FIG. 2 is a detail of the construction of the outer wall 7 and inner wall 6 of the containment carrier. The outer wall of the carrier is shown as a layer of polymers 7 which is a minimum of two (2) mil thick, made of a polymer with a melt index of 1.0; a density of 0.918 which produces a rated elongation break of 600 (ASTMD882) and an impact strength of 200 (ASTMD1709/A). The inner wall of the carrier 6 is a layer of polymers which is a minimum of two (2) mil thick, made of a polymer composed of an ethylene-vinyl acelate copolymer with a melt index of 0.50; a density between 0.923 and 0.932 and 5% red color concentrate. This combination produces an elongation break of 700 (ASTMD638) with an impact strength of 400 (ASTMD1709). The seal 4, the walls 6, 7 and the serration 5 is shown for illustration purposes.

Figure 3:
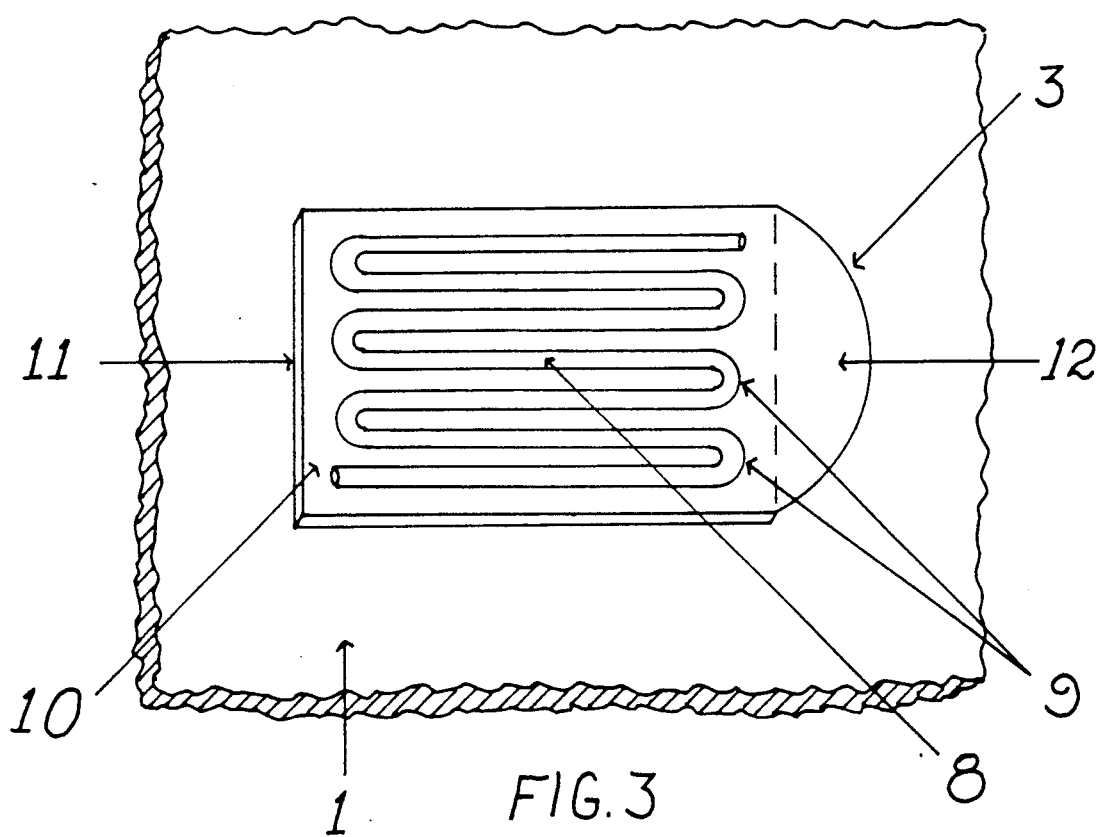
FIG. 3 and 4 are of the pouch which is the closure component. These drawings show the pouch in the closed and open position.

FIG. 3 is a schematic of the polyethlyene closure pouch 3. The pouch 3 is welded to the outer layer of the containment carrier 1. It contains a folded twelve (12) inch tie cord, 50 pound test, 9 of which a portion is welded to the back of the pouch 8 to insure the tie cord 9 remains attached to the containment carrier 1. The closure pouch 3 is constructed of polyethylene film. The back side of the pouch 11 is welded to the outer layer of the containment carrier 1. The front side of the pouch 10 is constructed with a tab 12 which when pulled from right to left FIG. 4, 10 and 12 opens, releasing the tie cord FIG. 4, 9 attached to the pouch 8.

Figure 4:
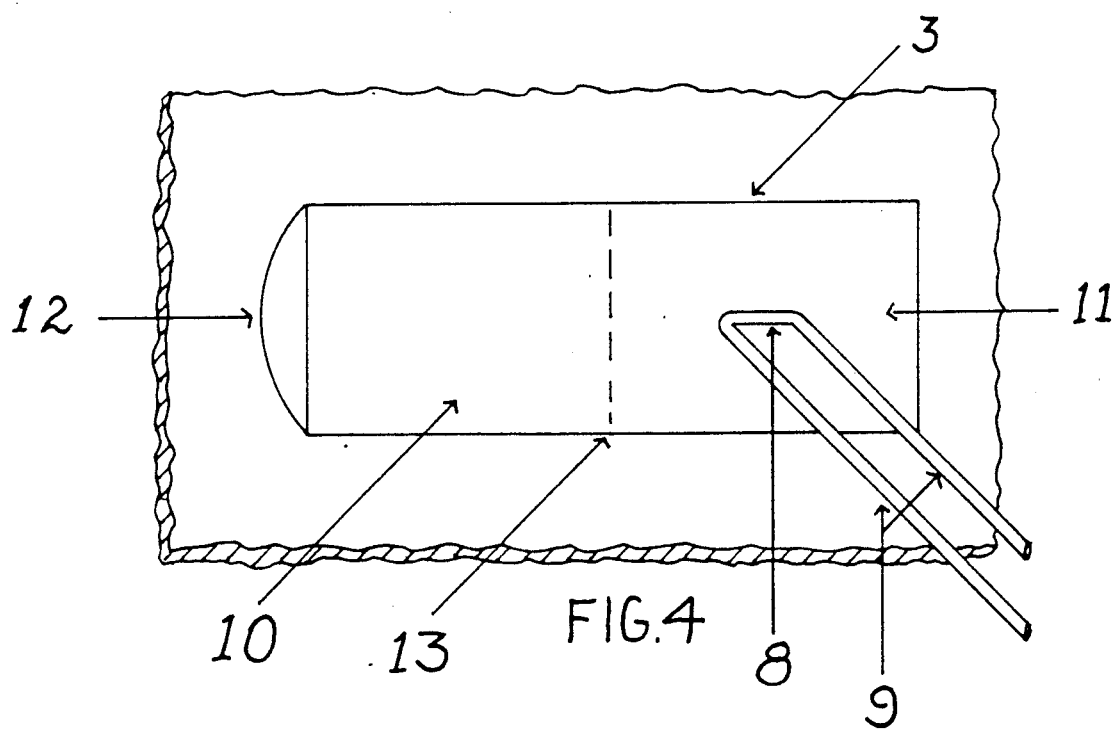

FIG. 4 illustrates the closure pouch 3 in the open position. The back side of the pouch 11 is welded to a segment of the tie cord while the tie cord 9 falls free for the closure procedure. The front side of the pouch 10 with the quick tab 12 stays adjoined to the bottom of the pouch at the fold line 13 to prevent litter. Once the closure system has been utilized and the container carrier is closed as identified in FIG. 6, 7, 8 and 9, the Infectious/Medical Waste Container Carrier is removed for incineration.

FIG. 5, 6, 7 and 8 graphically illustrates the four steps in the closure procedure.

Figure 5:
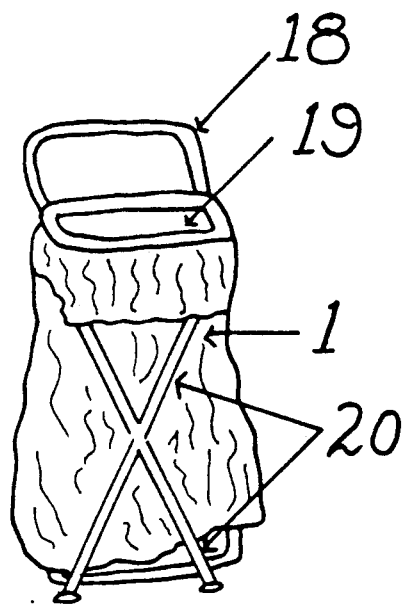
FIG. 5, 6, 7, and 8 are the steps required in the closure technique.
Figure 6:
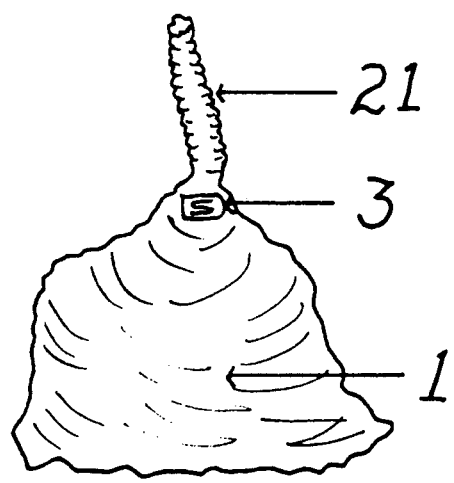
Figure 7:
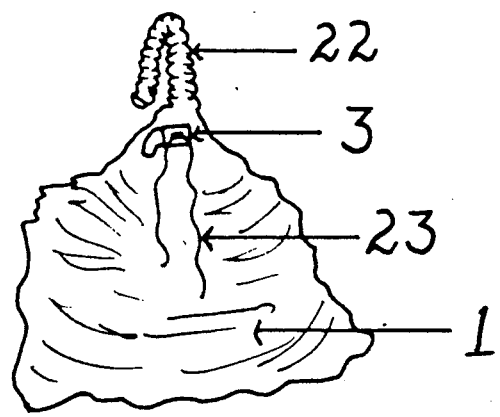

Step 1: FIG. 5 shows the containment carrier 1 positioned in the holder 20 with the holder's lid 18 and the containment carrier's opening 19 for deposit of the infectious waste.

Step 2: The infectious waste is deposited FIG. 5, 19 in the Infectious/Medical Waste Containment Carrier 1 which is removed from the holder FIG. 5, 20. The infectious waste is positioned in the lower portion of the containment carrier FIG. 6, 1 and the top of the containment carrier 21 is drawn together manually, twisted in a counter-clockwise direction until tight. The closure pouch 3 is then ready for opening.

Step 3: The Infectious/Medical Waste Containment Carrier 1, with the top of the containment carrier in a twisted manner FIG. 6, 21 configuration is then folded over FIG. 7, 22, the closure pouch 3 is opened, and the tie cord 23 falls free.

Figure 8:
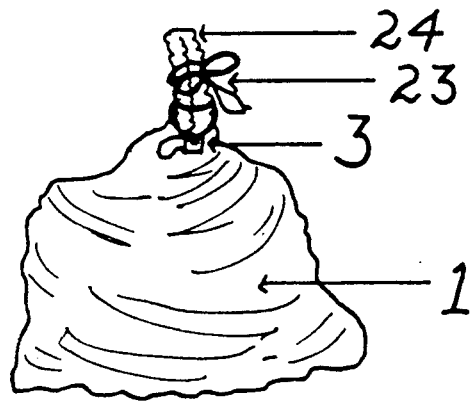

Step 4: FIG. 8 showes the Infectious/Medical Waste Containment Carrier 1 with the closure pouch 3 opened and the twisted top folded over 24. The closure pouch tie cord 23 is then wrapped around the twisted, folded-over top 24 of the containment container 1 and knotted tightly to insure the fail-proof closure. The Infectious/Medical Waste Containment Carrier is ready for removal to an incinerator.

Figure 9:
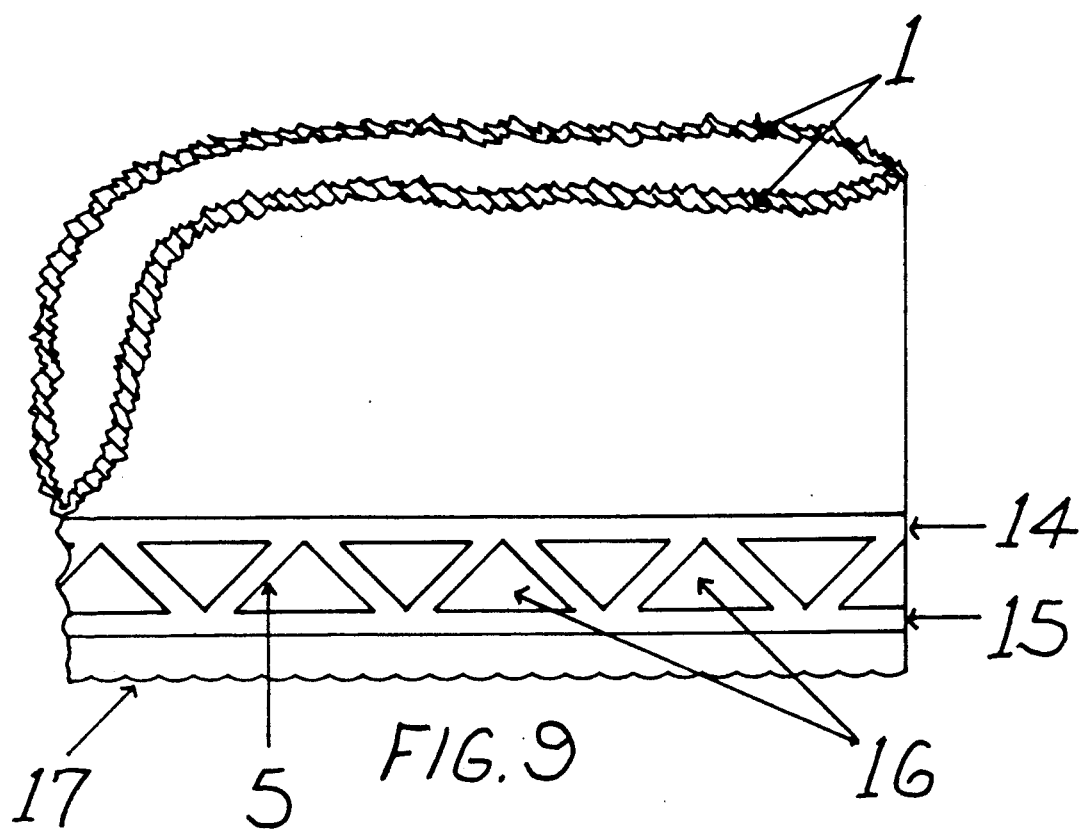
FIG. 9 is a detail of the seal which identifies the thermo-sealed bars and the air-pockets.

FIG. 9 illustrates the construction of the seal. The containment carrier 1 is closed at the bottom, just above the serration 5 by a dual thermo-sealed bar 14, 15, and 17 are the air-pockets 16. These air-pockets 16 add strength to the construction of the total seal FIG. 1, 4.

The invention claimed is:

1. A bag for infectious and medical waste containment comprising:
    (a) inner and outer walls of polyethylene;
    (b) a bottom seal consisting of dual thermo-sealed bars and spaced air-pockets between said thermo-sealed bars for reinforcement of the bottom seal;
    (c) a closed, polyethylene pouch thermo-sealed to the outer wall with a closure cord to close the bag contained within the pouch.

2. The bag of claim 1 wherein the outer wall is red in color.

3. The bag of claim 1 wherein the pouch includes a tab that is integral with and alongside an edge of a pouch wall for facilitating the opening of the pouch and releasing the closure therefrom.

4. The bag of claim 3 wherein the closure cord is welded to the inside of the pouch.

* * * * *